United States Patent
Fox et al.

(10) Patent No.: US 9,549,806 B2
(45) Date of Patent: Jan. 24, 2017

(54) BIORESORBABLE LARYNGOTRACHEAL STENT AND METHODS OF TREATMENT

(71) Applicant: Abbott Cardiovascular Systems Inc., Santa Clara, CA (US)

(72) Inventors: Julia C. Fox, San Carlos, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 51 days.

(21) Appl. No.: 14/458,121

(22) Filed: Aug. 12, 2014

(65) Prior Publication Data

US 2015/0045882 A1 Feb. 12, 2015

Related U.S. Application Data

(60) Provisional application No. 61/865,080, filed on Aug. 12, 2013.

(51) Int. Cl.
| | | |
|---|---|---|
| *A61F 2/20* | (2006.01) | |
| *A61F 2/04* | (2013.01) | |
| *A61L 31/16* | (2006.01) | |
| *A61L 31/14* | (2006.01) | |
| *A61F 2/82* | (2013.01) | |

(52) U.S. Cl.
CPC ............. *A61F 2/04* (2013.01); *A61L 31/148* (2013.01); *A61L 31/16* (2013.01); *A61F 2/20* (2013.01); *A61F 2/82* (2013.01); *A61F 2002/046* (2013.01); *A61F 2210/0004* (2013.01); *A61F 2230/0067* (2013.01)

(58) Field of Classification Search
CPC .................................. A61F 2/20; A61F 2/203
USPC .............................................................. 623/9
See application file for complete search history.

(56) References Cited

U.S. PATENT DOCUMENTS

| 9,180,029 B2 * | 11/2015 | Hollister ................. A61F 2/848 |
| 2008/0001333 A1 | 1/2008 | Kleine et al. |
| 2008/0275537 A1 | 11/2008 | Limon |
| 2011/0190871 A1 | 8/2011 | Trollsas et al. |
| 2011/0190872 A1 | 8/2011 | Anukhin et al. |
| 2014/0072610 A1 * | 3/2014 | Venkatraman .......... A61L 31/06 424/426 |
| 2014/0330377 A1 * | 11/2014 | Niklason ............. A61L 27/3633 623/9 |

(Continued)

OTHER PUBLICATIONS

Duerig et al., "An overview of superelastic stent design", Min Invas Ther & Allied Technol 9(3/4), pp. 235-246 (2000).

(Continued)

*Primary Examiner* — Suzette J Gherbi
(74) *Attorney, Agent, or Firm* — Squire Patton Boggs (US) LLP

(57) ABSTRACT

Bioresorbable stents for treating airway disorders and methods of treatment of the airway disorders using the bioresorbable stents are disclosed. Once implanted, the stents stabilize or maintain an airway lumen. The radial strength of the stents decreases with time which allows the airway to adjust from being artificially supported to a healed state without artificial support. The stent may be removed from the airway through bioresorption without intervention. The bioresorbable stents include a bioresorbable body having a shape that conforms or is conformable to the shape of the of airway lumen.

9 Claims, 6 Drawing Sheets

(56) References Cited

U.S. PATENT DOCUMENTS

| | | | |
|---|---|---|---|
| 2015/0094809 A1* | 4/2015 | Perrin | A61F 2/203 623/9 |
| 2015/0202074 A1* | 7/2015 | Gillis | A61F 5/56 128/848 |
| 2016/0022449 A1* | 1/2016 | Lim | A61F 2/885 623/9 |
| 2016/0051385 A1* | 2/2016 | Hollister | A61F 2/848 623/1.28 |

OTHER PUBLICATIONS

Meille et al., Definitions of tems relating to crystalline polymer (IUPAC Recommendations 2011), Pure Appl. Chem., vol. 83, No. 10, pp. 1831-1871 (2011).
Choi et al., "Pitfalls in laryngotracheal reconstruction", Arch. Otolaryngol Head Neck Surg. 125, pp. 650-653 (1999).
Makris et al., "Tracheobronchial stenting and central airway replacement", Curr. Opin. Pulm. Med. 13, pp. 278-283 (2007).
Simoni et al., "Microbiology of stents in laryngotracheal reconstruction", The Laryngoscope 114, pp. 364-367 (2004).

* cited by examiner

BIORESORBABLE LARYNGOTRACHEAL STENT AND METHODS OF TREATMENT

This application claims the benefit of U.S. Application Ser. No. 61/865,080 filed Aug. 12, 2013, which is incorporated by reference herein.

BACKGROUND OF THE INVENTION

Field of the Invention

This invention relates to bioresorbable implantable medical devices and methods of using such devices to stabilize or maintain an airway lumen during treatment of airway disorders.

Description of the State of the Art

This invention relates generally to treatment of laryngeal and tracheal stenosis with endoprostheses that are adapted to be implanted in the airway of an adult or child to stabilize or maintain the airway lumen. An "endoprosthesis" corresponds to an artificial device that is placed inside the body. "Stenosis" refers to a narrowing or constriction of a bodily passage or orifice. The endoprosthesis may stabilize or maintain the airway to facilitate restoring the airway lumen to a healthy or normal state and function. Laryngotracheal stenosis that is treatable by stenting has multiple causes. The most common factors for LTS are prolonged intubation usually associated with general anesthesia, external fracture of laryngeal, cricoid or tracheal cartilage structure, or subglottic stenosis. After surgical laryngeal reconstruction, a laryngotracheal stent is placed to stabilize the airway while it heals. The stent is temporary and the duration of stenting may be short on the order of 4-6 weeks, or longer than 2 months. The stent is not removed until the airway has sufficiently stabilized as premature removal can lead to airway collapse with resulting stenosis. Stabilizing an airway may correspond to permitting continuous unobstructed passage of air to the lungs. Airway disorders of various origins are treated with stents to stabilize or maintain the airway lumen. Stents, generally, are devices that hold open and sometimes expand a segment of an anatomical lumen such as an airway lumen, blood vessel, urinary tract, and bile ducts. A "lumen" refers to a cavity of a tubular structure. In addition to the conditions discussed below, any time the airway is opened to treat a disorder of the larynx, a stent can be considered for stabilization, scar prevention, or airway protection while the region heals.

Laryngotracheal stents, inserted after laryngotracheal reconstruction (LTR) to treat laryngotracheal stenosis, are most commonly used in children and young adults aged less than 20 years. Laryngotracheal stents are used in adults, primarily in the trachea, to relieve obstruction secondary to benign or malignant neoplasms.

Laryngotracheal stents are often used to keep the airway expanded after surgical reconstruction or trauma. Occasionally, laryngeal stents can be used for expansion of a diseased airway. Stenting in the tracheobronchial tree is usually used as a last resort for severe conditions such as recurrent carcinoma and severe tracheal collapse that results in periods of prolonged apnea.

The most common indication for laryngeal stenting follows reconstruction of laryngotracheal stenosis (LTS). Laryngeal stents can be used to keep the laryngeal lumen open and the reconstruction supported and stable. Occasionally, laryngeal stents are used following trauma to the larynx resulting in laryngeal fracture or injury. Stenting may help maintain lumen patency and prevent mucosal lacerations from forming obstructive scar tissue.

The first reason to use stents in cases of LTS is to support the larynx, after a reconstructive technique, often with some form of autologous cartilage, has been performed. A stent can be used to stabilize the cricoid plate once it has been divided anteriorly or posteriorly, with or without cartilage placement, to keep the complex in an expanded formation during healing. Stenting to help stabilize the laryngeal structure normally lasts for 2-6 weeks. It has been shown that when a cartilage graft is inserted, the minimum time necessary for a posterior cricoid split to heal in a distracted manner is 2 weeks. If stenting is performed for a shorter duration, the graft may prolapse into the lumen. For anterior graft placement only, stenting commonly lasts for a week or less.

The second reason for stent placement in LTS repair is to counteract scar contraction. Theoretically, this requires stenting for up to a 6-month period. In general, guidelines to determine the duration of stenting depend on the consistency of the stenosis, the anatomical distortion of the disease process, and the stability of the reconstructive areas.

Tracheal stenting may be used in the treatment of tracheal lesions, tracheomalacia, bronchomalacia, or stenosis that occurs following the resection of lesions.

The purpose of stenting for tracheal lesions varies from palliation, to cure, to stabilization while a reconstructive effort heals. Hence, the laryngotracheal stent primarily has a mechanical role. Use of the stent for delivery of a therapeutic agent is possible and useful agents to release would be antimicrobial agents to combat infection, antiproliferative agents to reduce obstructive scarring, and agents to promote healing. In adults, primary cancer of the tracheobronchial tree or cancer from the head, neck, or chest that extends into the tracheobronchial tree frequently causes lumen compromise and airway obstruction. The intraluminal component can be removed with laser treatment, mechanical debulking, electrocautery, brachytherapy, photodynamic therapy, or cryotherapy. A stent can then be placed to maintain the airway lumen following debridement to counteract collapse or edema. Alternatively, stents can be placed that help compress any lesion extending into the trachea or bronchi, without the need for debulking.

Stents have been used successfully to palliate patients with inoperable bronchogenic cancer, primary tracheal tumors, and metastatic malignancies. Placing a stent in a patient with a terminal illness allows that patient to breathe comfortably and prevents death from asphyxiation.

Tracheomalacia and bronchomalacia (sometimes called tracheobronchomalacia) may be primary or secondary in nature. These conditions usually occur in children, but they can be observed in adults. Tracheomalacia and bronchomalacia are termed primary if they arise from primary cartilage abnormalities of the trachea, such as immature formation of the cartilaginous rings in neonates or relapsing polychondritis in children and adults. Primary tracheomalacia is often observed with a tracheoesophageal fistula. Secondary tracheomalacia or bronchomalacia is caused by extrinsic compression from a structure in the mediastinum.

If tracheomalacia or stenosis occurs following the resection of lesions, stents can be placed in the trachea to prevent scarring or to provide support for the operated segment while it heals. In most situations, surgical correction as primary treatment for a disease process is preferred to stenting alone because complications are decreased. However, situations arise in which patients cannot undergo formal corrective surgery, and stent placement is the only way to prevent a severe apneic event or death.

Current laryngotracheal stents are durable devices, made of silicone, poly(tetrafluoroethylene) (PTFE, Teflon), or other polymers. These devices are removed after implant times ranging from 4 weeks to several months. FIGS. 1A-C depict commonly used devices, including the Montgomery stent, Montgomery T-tube and Aboulker stent, respectively.

If the stenosis is confined to the larynx (i.e., glottis, subglottis), stenting can be short- or long-term. Short-term stenting may be defined as stenting for less than 6 weeks. Long-term stenting is defined as stenting for more than 6 weeks.

Short term stenting for 6 weeks or less may be used because granulation tissue forms at the lower end of the stent above the tracheotomy, potentially leading to tracheal stenosis or collapse above the tracheotomy site. Short-term stenting may also be used for stabilization of cartilage grafts following LTR and/or for separation of mucosal surfaces during healing following laryngeal trauma, repair of web formation or atresia, or excision of a laryngeal lesion. Stents for these indications include Aboulker stents, silicone stents, Montgomery laryngeal stents, endotracheal tubes, and laryngeal keels.

In FIG. 1C, the representative (non-inclusive) samples demonstrate various sizes of Aboulker stents, ranging from 15 mm in diameter at the top to 3 mm in diameter at the bottom. These stents are hollow and are coated with PTFE.

The Montgomery Laryngeal Stent is a molded silicone prosthesis designed to conform to the normal endolaryngeal surface and is constructed of radiopaque implant grade silicone that is firm enough to support the endolarynx postoperatively, yet is soft and flexible enough to ensure a conforming fit while minimizing injury to soft tissues.

The Montgomery T-Tube is designed to maintain an adequate airway as well as to provide support in the stenotic trachea that has been reconstituted or reconstructed.

Use of durable stents usually requires removal of the stent after allowing a period of time for healing to take place. These devices have several complications including migration, fracture, keloid formation, granulation formation, and infection.

Inspection of FIGS. 1A-C reveals they are simple devices that are not expanded in place, are not fenestrated and have various levels of flexibility and compliance. As can be seen in FIG. 1AC, these devices come in a variety of sizes to match different anatomies and this is particularly driven by pediatric use. These devices are all inserted at the as-fabricated or final diameters and are not expanded once inserted in an airway.

Another challenge with these durable stents is selecting how long to keep them in place. LTR requires anterior and/or posterior cricoid splits, sometimes combined with cartilage tissue grafts. After the procedure, the stent is put into place to hold open the airway while healing occurs. The stent can also increase the stability of a graft and prevent scar contracture. Premature removal of the stent can lead to LTR failure.

SUMMARY OF THE INVENTION

Embodiments of the present invention include a method of treating an airway disorder in a patient in need of treatment thereof, comprising: providing a bioresorbable non-expandable stent; and maintaining an airway in a desired configuration by disposing the stent within the airway of a patient having an airway disorder, wherein an initial radial strength of the stent allows it to maintain the desired configuration of the airway to allow healing of the airway, wherein the radial strength of the stent decreases with time due to bioresorption of the stent allowing the airway to adjust from being artificially supported to a healed state without artificial support of the stent.

Embodiments of the present invention include a stent for treating an airway lumen in a patient that has an airway disorder comprising a bioresorbable tubular body that is not radially expandable having an external profile that is conformable to an airway geometry of the patient, wherein the body is composed at least in part of a bioresorbable polymer.

Embodiments of the present invention include a method of treating an airway disorder in a patient in need of treatment thereof, comprising: providing a bioresorbable radially expandable bioresorbable scaffold; and maintaining the airway lumen at a desired configuration by radially expanding the scaffold within the airway to the desired configuration, wherein an initial radial strength of the scaffold allows it to maintain the airway in the desired configuration of the airway to allow healing, wherein the radial strength of the scaffold decreases with time due to bioresorption of the scaffold allowing the airway to adjust from being artificially supported to a healed state without artificial support of the scaffold.

Embodiments of the present invention include a medical device for treating an airway lumen of a patient having an airway disorder: a radially expandable stent comprising a tubular body expandable from a reduced state to a deployed state in an airway, wherein the tubular body conforms to a geometry of the airway in the deployed state, where the tubular body is composed at least in part of a bioresorbable polymer.

INCORPORATION BY REFERENCE

Figure 1A:
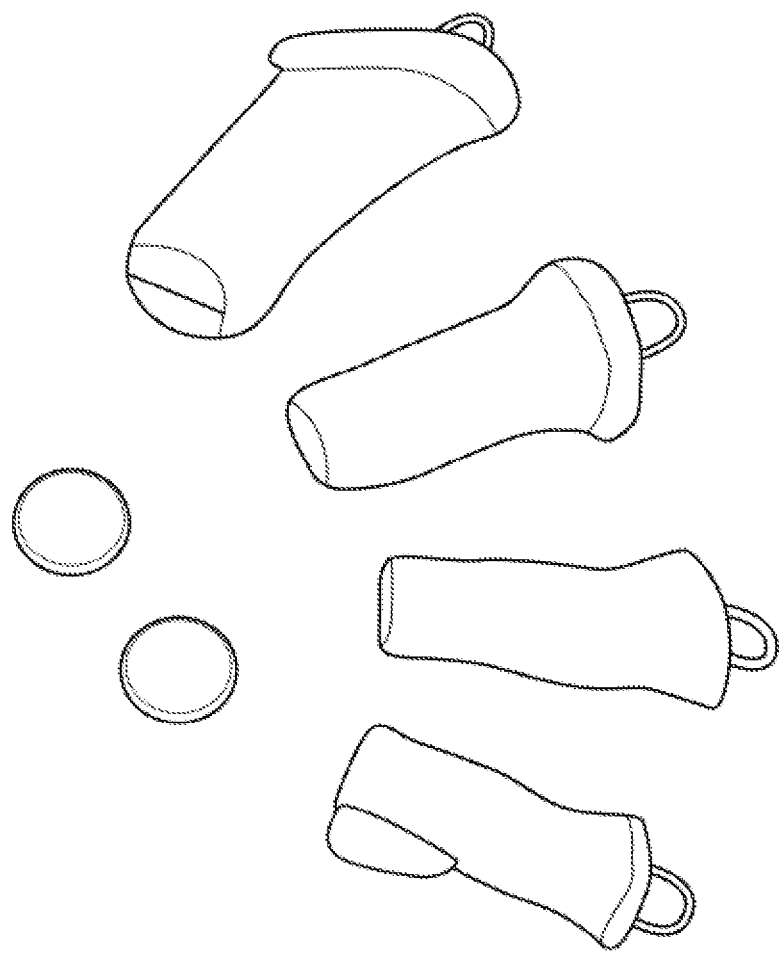
FIG. 1A depicts Montgomery stents.

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF THE INVENTION

Embodiments of the present invention include bioresorbable stents for treating airway disorders and methods of treatment of the airway disorders using bioresorbable stents to stabilize or maintain an airway lumen. The bioresorbable stent includes a bioresorbable body having a shape that conforms or is conformable to the shape of the airway lumen. The bioresorbable stent is implanted in an airway of a patient such as the larynx or trachea to temporarily support and maintain the airway lumen at a desired size.

As discussed in more detail below, the stent can be a scaffold or stent scaffold which is a type of fenestrated tube. "Fenestrated" refers to holes or gaps extending partially or completely through the wall of a tube. A scaffold is composed of a plurality of interconnected structural elements or struts arranged to form a tubular geometry. The arrangement of the structural elements allows the scaffold to be radially expandable or compressible/contractible.

The stent may further include an active agent associated with the device. Release of an active agent from the device can be accomplished by incorporation of the agent throughout the device in a monolithic fashion, or the agent can be applied via a coating. Active agents are typically released although certain agents may be immobilized on the device surface. Coatings which contain no pharmacologically active agent, but which are present to provide a lubricious surface, or a mucoadhesive surface can be affixed to the laryngotracheal stents or scaffold.

Embodiments include stents that are partially bioresorbable or completely bioresorbable. The bioresorbable body eventually disappears from the implant site due to one or more degradation mechanisms.

A bioresorbable laryngotracheal stent or scaffold may eventually resorb and facilitate normalization of airway function in patients with pathologies including laryngotracheal stenosis, glottic stenosis, subglottic stenosis, bronchogenic tumors, tracheomalacia, bronchomalacia, and tracheal trauma.

The laryngotracheal scaffold may be made partially or completely out of a bioresorbable material. Embodiments can include implants fabricated from biodegradable, bioabsorbable, bioresorbable, and/or bioerodible materials such as bioabsorbable polymers, or bioerodible metals that can be designed to completely erode only after the clinical need for them has ended. The terms biodegradable, bioresorbable, bioabsorbable, and bioerodible have distinct definitions in the scientific literature, but are often used interchangeably. The term bioresorbable polymer refers to a polymer which is designed to become discontinuous in the body and whose degradation products are metabolized. The scaffold may completely disappear in 1 to 30 months, 2 to 12 months, 3 to 24 months, 3 to 12 months, 6 to 30 months, 6 to 48 months, or 6 to 12 months.

Figure 2:
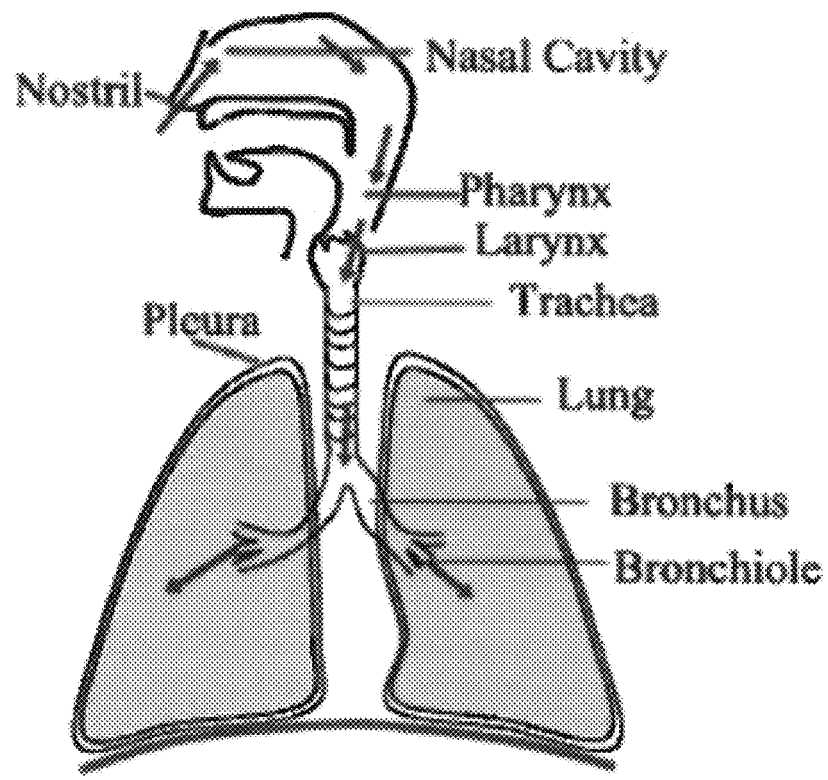
FIG. 2 depicts a schematic of the respiratory pathway.

FIG. 2 depicts a schematic of the respiratory pathway. The arrows show the path of inhaled air through the components of the pathway. Air enters through the nostrils and flows through the nasal cavity, or through the mouth, where both passage ways flow to the pharynx, larynx, and trachea. The trachea bifurcates into two bronchi that provide two separate pathways for air into the lungs. Air is dispersed through the lungs in the bronchioles.

The pharynx is the part of the throat situated immediately inferior to (below) the mouth and nasal cavity, and superior to the esophagus and larynx. The human pharynx is conventionally divided into three sections: the nasopharynx (epipharynx), the oropharynx (mesopharynx), and the laryngopharynx (hypopharynx). The pharynx is part of the digestive system and also the respiratory system; it is also important in vocalization.

The larynx is an organ in the neck involved in breathing, sound production, and protecting the trachea against food aspiration. The larynx is found in the anterior neck at the level of the C3-C6 vertebrae. It connects the inferior part of the pharynx (hypopharynx) with the trachea. The laryngeal skeleton consists of nine cartilages: three single (epiglottic, thyroid and cricoid) and three paired (arytenoid, corniculate, and cuneiform). The hyoid bone is not part of the larynx, though it is connected to it. The larynx extends vertically from the tip of the epiglottis to the inferior border of the cricoid cartilage. Its interior can be divided in supraglottis, glottis, and subglottis.

The diameter of an adult larynx may be between approximately 2 and 5 cm. For example, the average measurements of the adult larynx are as follows:

|  | In males | In females |
|---|---|---|
| Length | 44 mm | 36 mm |
| Transverse diameter | 43 mm | 41 mm |
| Antero-posterior diameter | 36 mm | 26 mm |
| Circumference | 136 mm | 112 mm |

The trachea or windpipe is a tube that connects the pharynx and larynx to the lungs, allowing the passage of air. It is lined with pseudostratified ciliated columnar epithelium cells with goblet cells that produce mucus. This mucus lines the cells of the trachea to trap inhaled foreign particles that the cilia then waft upward toward the larynx and then the pharynx where it can be either swallowed into the stomach or expelled as phlegm. The trachea has an inner diameter of 2 to 2.5 cm and a length of 10 to 16 cm. It commences at the lower border of the larynx, level with the sixth cervical vertebra, and bifurcates into the primary bronchi at the vertebral level of thoracic vertebra T5, or up to two vertebrae lower or higher, depending on breathing. There are fifteen to twenty incomplete C-shaped cartilaginous rings that reinforce the anterior and lateral sides of the trachea to protect and maintain the airway, leaving a membranous wall (pars membranacea) dorsally without cartilage. The trachealis muscle connects the ends of the incomplete rings and contracts during coughing, reducing the size of the lumen of the trachea to increase the air flow rate. The esophagus lies posteriorly to the trachea. The cartilaginous rings are incomplete to allow the trachea to collapse slightly so that food can pass down the esophagus. A flap-like epiglottis closes the opening to the larynx during swallowing to prevent swallowed matter from entering the trachea.

Trachea and laryngeal stenting with a bioresorbable stent (scaffold) offers several potential benefits. First, the bioresorbable stent has a variable radial strength with time as a consequence of the resorption process. Second, the use of a bioresorbable stent avoids the requirement of removal of the stent. Third, the size of the stent can be customized for particular airways and patients.

A bioresorbable stent is designed so that it is initially strong, providing the radial support the trachea needs during healing. The initial radial strength is at least high enough to maintain the trachea at a target diameter. The radial strength has an initial value at implantation or at time=0. The radial strength of the stent decreases with time due to decrease in polymer molecular weight and resorption of the stent material, allowing the tracheal lamina and cartilaginous rings to heal. The trachea thus gradually adjusts from a state of being artificially under stress from the stent support to a healed state without artificial support of the stent. This avoids the stress shielding and sudden loss in radial support which occurs with the current durable devices when the durable device is removed.

A bioresorbable stent may have selected radial strength versus time profile. This profile can be tuned by the choice of resorbable polymer, its initial molecular weight, degree of crystallinity, concentration of oligomers and monomer, as well as other chemical and microstructural parameters. The initial molecular weight of the bioresorbable polymer of the stent may be 20 to 50 kDa, 50 to 70 kDa, 70 to 100 kDa, 100 to 200 kDa, 200 to 300 kDa, or greater than 300 kDa.

One useful profile of radial strength consists of a plateau phase where the strength only decreases slightly with time followed by a second phase of faster radial strength loss. The radial strength during the plateau phase may decrease by 10% or by less than 10%, by 50% or by less than 50%, by 1 to 5%, by 5 to 10%, by 10 to 50%, or 40 to 50% of the initial radial strength. The duration of the plateau phase determines the interval of strength adequate for clinically useful radial support. This plateau phase may last for only 1 week, for 1-2 weeks, 2-4 weeks, 3-6 weeks, 4-8 weeks, 8-12 weeks, 12-24 weeks, or longer than 24 weeks. During the second phase, the radial strength may decrease to more than 50%, or more narrowly, 50 to 90%, 50 to 60%, 60 to 80%, or 80 to 90% of the initial radial strength. The time period of the decrease may be 5 hr 10 hr, 10 hr to 1 day, 1 to 2 days, 2 to 5 days, or a least 1 week.

An alternative description of the plateau phase is that at the end of this phase, the radial strength drops more rapidly and a time point corresponding to a 50% decrease relative the scaffold's initial strength may be defined. This time for the scaffold to lose 50% of its radial strength may be only 1 week, 1-2 weeks, 2-4 weeks, 3-6 weeks, 4-8 weeks, 8-12 weeks, 12-24 weeks, or longer than 24 weeks. As described in an embodiment above, such a device could still be physically removed at the end of the therapy spanning 4 weeks to 6 months or more.

Anisotropic behavior of the stent, where the radial and axial strength are not the same on a dimensional basis can be achieved by stent design, or processing of the polymer, such as by polymer or polymer crystallite orientation. Another means is by structural elements oriented axially and radially, each of which has a different strength or resorption with time profile. These strategies can be employed for the stent to lose radial strength while adequate axial strength is maintained for stent removal at a later time point.

The stent holds open or maintains patency of an airway. To achieve this, the stent must be capable of withstanding the structural loads, namely radial compressive forces, imposed on the stent as it supports the walls of a vessel, and both radial and axial fatigue from breathing, swallowing and eating. Radial strength, which is the ability of a stent to resist radial compressive forces, relates to a stent's radial yield strength and radial stiffness around a circumferential direction of the stent. A stent's "radial strength" (for purposes of this application) may be understood as the compressive loading, which if exceeded, creates a stress condition resulting in the stent diameter not returning to its unloaded diameter, i.e., there is irrecoverable deformation of the stent. See, T. W. Duerig et al., Min Invas Ther & Allied Technol 2000: 9(3/4) 235-246. When the radial yield strength is exceeded the stent is expected to deform more significantly and only a minimal force is required to cause further deformation. Radial strength is measured either by applying a compressive load to a stent between flat plates or by applying a circumferential or radial load to the stent.

As discussed above, one of the advantages of the bioresorbable tracheal or laryngeal stent is that it can avoid the requirement for removal at some future time point. The stent is placed by the physician in the airway and then degrades or resorbs over time which results in removal of the stent from the implant site, obviating the need for a future medical or surgical removal procedure.

The incentive for this capability depends on the patient due to the ease of accessing the trachea and the fact that after LTR, current stents are inspected every 3-4 weeks to assess a variety of healing aspects. However, predictable and safe resorption of the scaffold would make the more challenging stent removal step unnecessary. Alternatively, after the stent radial strength of the stent has slowly decreased to a minimum, and underlying airway structures assumed their physiological roles, the bioresorbable laryngotracheal stent may be optionally removed. Unlike endovascular stents placed in an artery or vein, laryngotracheal stents do not become encapsulated in the airway wall.

The prevailing mechanism of degradation of a bioresorbable polymer is chemical hydrolysis of the hydrolytically susceptible polymer chain or backbone. In an ideal bulk eroding polymer, the polymer is chemically degraded throughout the entire polymer volume due to diffusion of moisture into the polymer bulk. As the polymer degrades, the molecular weight decreases. The reduction in molecular weight eventually results in a decrease in mechanical properties such as strength and stiffness of the polymer material. The radial strength of a stent made of a bioresorbable polymer will decrease as the strength of the polymer decreases.

During the initial phase of molecular weight reduction, there may be little or no impact on the mechanical strength, and thus the radial strength of the stent. This corresponds to the plateau phase described above. When the molecular weight is sufficiently low, the strength of the stent polymer and radial strength of the stent start to decrease. Therefore, during the initial phase of molecular weight decrease with little or no decrease in strength or radial strength, a bioresorbable stent functions like a current durable polymer stent. If a more continuous decrease in radial strength is desired, and it is desirable for the stent strength to begin decreasing soon after implantation, this may be accomplished by using polymers with a very broad molecular weight distribution. For example, the radial strength may decrease by 5 to 10% per week or month.

Many bioresorbable polymers become softer and more flexible as the molecular weight decreases. A stent that starts out rigid but becomes more rubbery with degradation would allow the scaffold to be ultimately expectorated, which refers to coughing up and ejecting from the mouth. The bioresorbable stent material may become a gel or thick syrup at which point expectorating would be correspond to or be analogous to coughing up phlegm.

Alternatively, some bioresorbable polymers become softer and eventually becoming a viscous liquid. The deep lung is equipped with aveolar macrophages which remove normally aspirated particles. Low molecular weight bioresorbable polymer could be readily phagocytized and removed by these cells. Therefore, such a viscous liquid could be absorbed in the lungs, swallowed, or expectorated.

The decrease in strength of scaffold material from resorption may result in the formation of discontinuities in the scaffold. This leads to a further reduction in radial strength of the scaffold.

Polymer characteristics that facilitate a softening degradation mechanism include a low glass transition temperature and a low crystallinity. The larnygotracheal scaffold may be made partially or completely of a bioresorbable polymer with a low glass transition temperature and a low crystallinity. The bioresorbable polymer of the bioresorbable larnygotraceal stent may be completely amorphous (0% crystallinity), less than 5% crystallinity, less than 10% crystallinity, less than 20% crystallinity, less than 30% crystallinity, 5 to 10% crystallinity, 5 to 15% crystallinity, 10 to 15% crystallinity, 10 to 20% crystallinity, or 10 to 30% crystallinity.

The bioresorbable larnygotracheal stent may include or be formed from a polymer with a Tg below human body temperature or 37° C. The Tg may correspond to a dry state of the polymer or in a hydrated or wet state in water, simulated body fluid, or body fluid. The wet state may correspond to the polymer in the water or fluid for 1 hr, at least 1 day, 1 to 5 days, or 5 days for more. Exemplary polymers that may be amorphous or have a low crystallinity are poly(D,L-lactide), poly(D,L-lactide-co-caprolactone), poly(D,L-lactide-co-glycolide), poly(glycolide-co-caprolactone), poly(L-lactide-co-D,L-lactide). For copolymers, the ratio of the two or more monomers may be selected to maintain a selected low crystallinity in any of the ranges disclosed herein. Normally crystalline polymers such as poly(L-lactide) (PLLA) or poly(glycolide) may be processed to be amorphous by, for example, rapid quenching following thermal processing. Block copolymers with PEG and mucoadhesive components are also possible.

The bioresorbable polymer of the invention may have one or any combination of properties described below. The bioresorbable polymer may have an elongation at break greater than 30%, 50%, 80%, 100%, 500%, or above 500%. The bioresorbable polymer may have a modulus of elasticity less than 1.5 GPa, 1 GPa, or 0.5 GPa, or can be 0.5 GPa to 1 GPa at 25° C., 37° C., or in a range of 25 to 37° C. Additionally, the bioresorbable polymer may have a Tg less than body temperature or 37° C., less than 25° C., or less than 0° C.

The bioresorbable larnygotracheal stent may include or be formed from a polymer that is rigid above 37° C. Such polymers may have a Tg above human body temperature or 37° C. The polymer may have an elongation at break less than 20%, 10%, 5%, or 3%. The polymer may have a modulus of elasticity greater than 3 GPa, 5 GPa, or 7 GPa. Additionally, the polymer may have a Tg greater than human body temperature or 37° C., or greater than 10° C. or greater than 20° C. above human body temperature or 37° C. The polymer of the invention may have one or any combination of such properties.

The stent may be made of a polymer that is a blend or copolymer of a polymer that has rigid properties and polymer with a Tg below 37° C. The rigid polymer may 80 to 90, 90 to 95, or 95 to 99% (wt % or mol %) of the blend or copolymer.

Rigid bioresorbable polymers include PLLA, poly(D-lactide) (PDLA), poly(glycolide0, and poly(L-lactide-co-glycolide) (PLGA). The PLGA includes those having a mole % of (LA:GA) of 85:15 (or a range of 82:18 to 88:12), 95:5 (or a range of 93:7 to 97:3), or commercially available PLGA products identified being 85:15 or 95:5 PLGA.

The laryngotracheal stent may include several features including biocompatibility, flexibility for deliverability, radiopaque markers for fluoroscopic visualization during scaffold positioning, radial strength sufficient to maintain airway patency, design features such as ridges, flanges, barbs, hooks or scales to control scaffold migration, and availability in multiple sizes.

The initial radial strength of the stent may be greater than 35 kpa, 55 kpa, 70 kpa, 90 kpa, or 100 kpa. The radial strength of the stent may be 35 to 100 kpa, 35 to 55 kpa, 55 to 70 kpa, or 70 to 100 kpa. The radial strength ranges or values referred to anywhere in the application may refer to an implanted in vivo state or bench tests in a saline solution at 37° C. The radial strength may correspond to an as-fabricated state or a deployed state from a crimped or reduced state.

The laryngotracheal stent may also include a coating to help secure the stent in place and deliver a drug to the local site. Infection is a serious issue for laryngotracheal stents that may be mitigated with a drug coating on the bioresorbable stent. This is because the stents are placed in a septic environment with constant exposure to airborne microbes. The trachea is lined with a ciliated epithelial layer of cells. These cells secrete mucus and constantly sweep the mucus layer upwards so that it may be swallowed down the esophagus. Laryngotracheal stents can interfere with this self-cleaning flow and offer a synthetic surface for microbial colonization. Consequently, the bioresorbable laryngotracheal scaffold can have a coating that releases an antibiotic or broad spectrum antimicrobial agents to reduce infection. The antimicrobial agent may also be incorporated into the body of the scaffold.

Useful antimicrobial agents would include triclosan, chlorhexidine gluconate, iodine compounds, silver salts, silver sulfadiazine, amoxicillin, beta lactamase inhibitors, sulphonamides, cephalosporins, aminopenicillins, penicillins, cefpodoxime, levofloxacin, clindamycin, and piperacillin-tazobactam. To prevent cellular proliferation and formation of granulation tissue useful antiproliferative agents are sirolimus, everolimus, zotarolimus, rapamycin derivatives, deforolimus umirolimus, and temsirolimus. Antiinflammatory agents may also find utility in reducing formation of granulation tissue. Agents to promote healing of the airway after LTR include growth factors and vitamin E. A non-drug eluting coating may be present to promote stent securement and this may be a mucoadhesive coating. Such coatings are known and may comprise poly(acrylic acid), poly(methacrylic) acid, chitosan sodium alginate, cellulose derivatives, and thiolated polymers which are immobilized or strongly associated with the laryngotracheal stent surface. Alternatively, a lubricious coating may be applied to the surface of the stent to enhance ease of placement. Coatings consisting of or including immobilized, or crosslinked, poly(ethylene oxide), poly(vinyl pyrollidone), or hyaluronic acid can be used for lubricity.

Indications for the bioresorbable tracheal stent (scaffold) may include laryngotracheal stenosis, glottic stenosis, subglottic stenosis, bronchogenic tumors, tracheomalacia, bronchomalacia, and tracheal trauma.

In certain embodiments, the bioresorbable laryngotracheal stent is not radially expandable, for example, by a catheter balloon. In such embodiments, the non-expandable bioresorbable stent is delivered to an airway lumen and positioned at a site within an airway. In such embodiments, the stent has an as-fabricated or delivery diameter that is the equal to the deployment or implantation diameter. The diameter can refer to either inside or outside diameter of the stent.

An initial radial strength of the stent allows it to maintain the airway in a tubular configuration of the stent to allow healing in the supported state. The radial strength of the stent decreases with time due to bioresorption of the stent which allows the airway to adjust from a state of being artificially supported to a healed state without artificial support of the stent. The transition from a stressed healing state to a healed stress-free state due to bioresorption occurs gradually in contrast to interventional removal of the stent from the airway.

The stent may be a tube that may be hollow or not hollow made partially or completely of a semi-flexible bioresorbable polymer. A semi-flexible bioresorbable polymer may correspond a polymer having a Tg<37° C. in a hydrated state. It may or may not be fenestrated. The fenestration may enhance fixation of the scaffold in the lumen. In some embodiments, the stent may not be radially expandable or contractable. The stent may have a diameter designed to match a particular patient airway lumen and patient anatomy. The stent may have a diameter of 4 mm to 10 mm, 3 mm to 25 mm, or 2 mm to 50 mm.

The tube can be formed by extrusion or other process such as injection molding. The extruded tube can be made at the as-fabricated diameter. Alternatively, the extruded tube diameter can made to be less than the as-fabricated diameter and expanded to the as-fabricated diameter to impart circumferential orientation of polymer chains to increase the radial strength of the tube or scaffold. The tube may additionally or alternatively be axially drawn or stretched to increase orientation of polymer chains in the longitudinal direction.

A blow molding process may be used to radially expand the tube. In blow molding a tube is positioned within a cylindrical mold. The pressure is increased within the mold to radially expand the tube and the cylindrical mold controls the diameter of the expanded polymeric tube by limiting the expansion to the inside diameter of the cylindrical mold. The inside diameter may be the desired as-fabricated diameter. The mold and tube may be heated above ambient temperature and preferably above the Tg of the polymer of the tube.

The degree of radial expansion based on the inside diameter of the extruded and expanded tubes may be at least 50%, at least 100%, at least 200%, at least 300%, at least 400%, 50 to 100%, 100 to 200%, 200 to 300%, or 300 to 400%. The percent Radial Expansion (% RE) can be defined as (IDex/IDorig−1)×100%, where IDex is the inside diameter of an expanded tube and IDorig is the original inside diameter of the tube prior to expansion.

In some embodiments, the as-fabricated diameter may have a variable diameter along the tube axis. The variable diameter may be adapted to conform or match the laryngotracheal airway lumen. An example of a variable diameter tube is a tapered tube with a larger diameter at one end and smaller diameter at another and a diameter that tapers or decreases from the larger diameter to the smaller diameter. The tapering may be linear or straight. Alternatively, the tapering may be nonlinear. A nonlinear tapering may be a concave profile in which the diameter decreases faster than linear. A nonlinear tapering may also be convex in which the diameter increases initially and then decreases down to the diameter at the smaller diameter end.

A variable diameter may also be an oscillatory axial profile in which the diameter increases and decreases. The oscillatory axial diameter profile may be designed to match the portion of the trachea with the cartilaginous rings.

Figure 3:
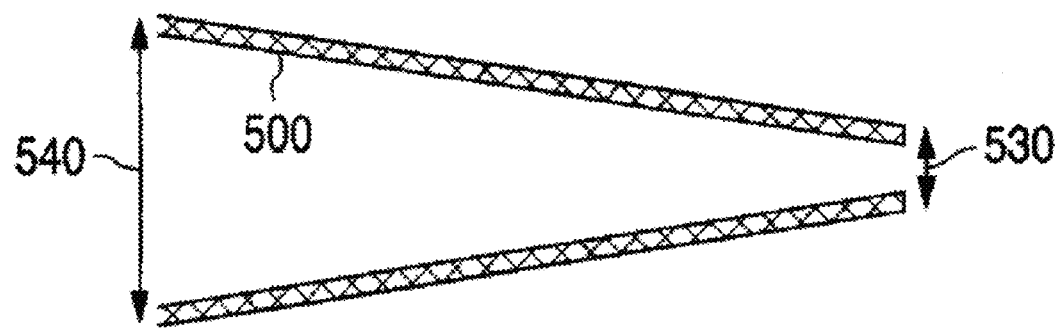
FIG. 3 depicts a tapered tube.

FIG. 3 depicts a tapered tube 500 with a diameter tapering from a larger diameter 540 to a smaller diameter 530 along its length. Such a tube can be formed by injection molding or by blow molding a uniform diameter tube in a tapered mold. A blow molding process is described in US2008-0001333.

Figure 1B:
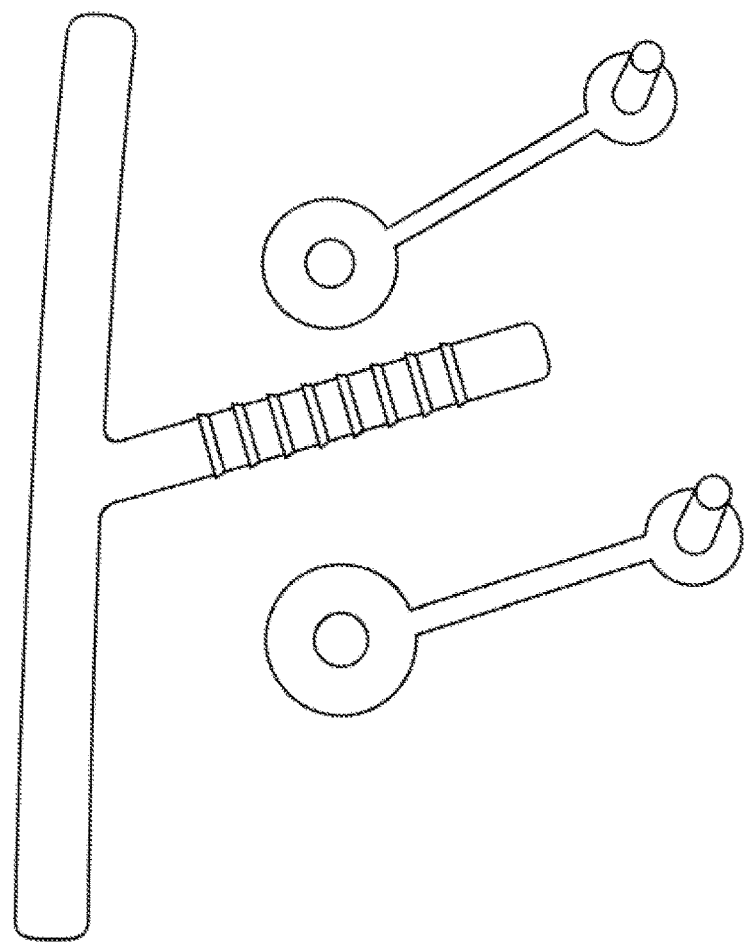
FIG. 1B depicts a Montgomery T-tube.
Figure 1C:
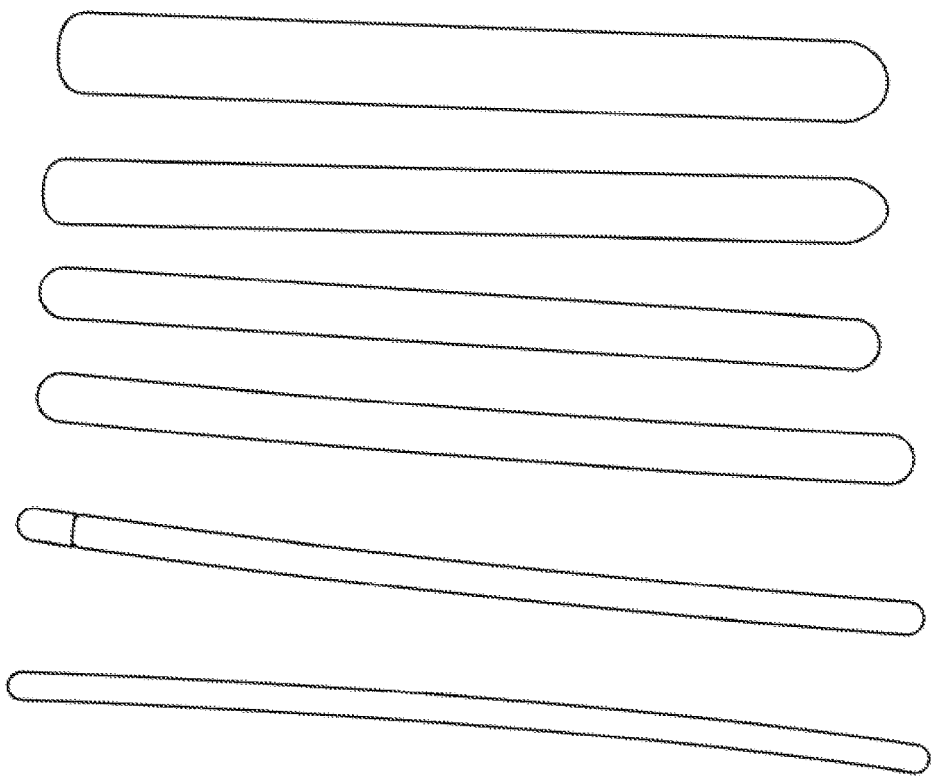
FIG. 1C depicts Aboulker stents.

As can be seen in FIGS. 1A-C, current devices for treating airway disorders come in a variety of sizes to match different anatomies and this is particularly driven by pediatric use. These devices are not radially expandable of contractible and are all inserted at the final or as-fabricated diameter.

Other embodiments include radially expandable bioresorbable scaffolds that have the ability to conform to an airway anatomy due to a variable or localized expansion or variable deployment diameter. The radially expandable scaffold can be balloon expandable, self-expandable or a combination of both. A radially expandable scaffold may include serpentine rings of structural elements that open during expansion. The serpentine rings include an alternating series of crests and troughs. The structural elements bend inward at the crests and troughs to allow the scaffold to radially contract and bend outward at the crests and troughs to allow the scaffold to radially expand. Each ring is connected to neighboring rings by two or more links. By being balloon expandable, the bioresorbable laryngotracheal scaffold deployed diameter can be custom sized to the patient's anatomy.

A method of treatment with a radially expandable scaffold includes delivering the scaffold to an implant site in a reduced delivery configuration. The scaffold may be reduced from an as-fabricated diameter to a delivery configuration. The reduced profile scaffold may be over a support such as a catheter balloon. The scaffold is deployed at the implant site in the airway by radially expanding the scaffold. In the case of a balloon expandable scaffold, the balloon is inflated and expanded to expand the stent. In the case of a self-expanding scaffold, the scaffold is placed in position at a restrained diameter and then deployed typically by retraction of a sheath that restrains the stent from self expanding. An initial radial strength of the scaffold allows it to maintain the airway in an expanded configuration of the airway to allow healing. The radial strength of the scaffold decreases with time due to bioresorption of the scaffold allowing the airway to adjust from being artificially supported to a healed state without artificial support of the scaffold.

The laryngotracheal airway tract is not simply a straight pipe of uniform diameter, it has curvature and variation in diameter. A radially expandable device can conform to the airway tract's geometric anatomy. The deployed stent may be touched up by expanding a dilatation balloon in specific regions for better apposition to the wall of the airway. As a result, the deployed diameter can vary along the axis of the airway lumen.

The geometry of the scaffold can be an open-cell structure or closed cell structure. The patterns can be formed through laser cutting a tube formed by, for example, extrusion. In a balloon expandable device, when the device is crimped from a fabricated diameter to a crimped or delivery diameter onto a balloon, structural elements plastically deform at the crests and troughs. Aside from incidental recoil outward, the scaffold retains a crimped diameter without an inward force on the crimped device due to the plastically deformed structural elements. When the device is expanded by the balloon, the structural elements plastically deform. The device is expanded to and retains an intended deployment diameter or more generally, deployment configuration. There may be incidental recoil inward due to inward pressure from the vessel, stress relaxation, or both. At the final deployed configuration, the scaffold may not exert any chronic outward force, which is a radial outward force exerted by the device in excess of the radial inward force exerted by the vessel on the device.

In the case of a self-expandable scaffold, when the scaffold is crimped from a fabricated diameter to a crimped or delivery diameter onto a support, which may be a balloon, structural elements deform elastically. Therefore, to retain the scaffold at the crimped diameter, the scaffold is restrained in some manner with an inward force, for example with a sheath or a band. The crimped scaffold is expands to an intended expansion or deployment diameter by removing the inward restraining force which allows the device to self-expand to the intended deployment diameter or configuration. The structural elements deform elastically as the device self-expands. If the final expansion diameter is the same as the fabricated diameter, the scaffold does not exert any chronic outward force. If the final expansion diameter is less than the fabricated diameter, the scaffold does exert a chronic outward force. The geometry of the self-expandable scaffold can be a helical construct including a set of spiral coils formed through laser cutting, or it can also be like a coil formed through weaving extruded and annealed fibers. Otherwise, the geometry of the self-expandable scaffold can be similar to those of current vascular stents which includes or consists of a series of interconnected struts.

The geometric structure of a radially expandable scaffold is not limited to any particular pattern or geometry. The scaffold can have a tubular structure that is composed of a plurality of ring struts and link struts. The ring struts form a plurality of cylindrical rings arranged about the cylindrical axis. The rings are connected by the link struts. The scaffold includes an open framework of struts and links that define a generally tubular body with gaps in the body defined by the rings and struts.

A thin-walled cylindrical tube may be formed into this open framework of struts and links by a laser cutting device that cuts such a pattern into a tube that may initially have no gaps in the tube wall. The scaffold may also be fabricated from a sheet by rolling and bonding the sheet to form the tube.

Figure 4:
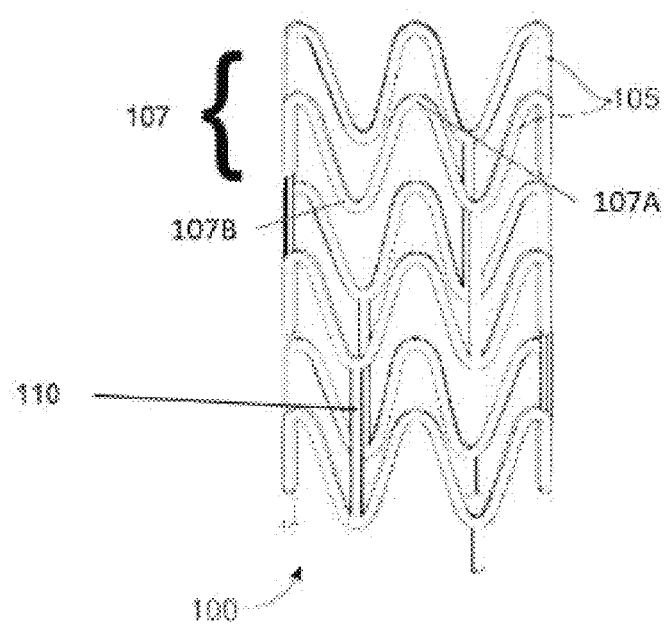
FIG. 4 depicts a view of an exemplary scaffold which includes a pattern or network of interconnecting structural elements.

FIG. 4 depicts a view of an exemplary scaffold 100 which includes a pattern or network of interconnecting structural elements 105. FIG. 4 illustrates features that are typical to many stent patterns including cylindrical rings 107 with alternating crests 107A and troughs 107B connected by linking elements 110. The cylindrical rings are load bearing in that they provide radially directed force in response to an inward force on the scaffold. The linking elements generally function to hold the cylindrical rings together. Exemplary scaffolds are disclosed in US2008/0275537, US2011/0190872, and US2011/0190871.

An effective amount of active agents or drugs, such as an antimicrobial agent, can be included or incorporated in the implant in various ways. The drug may be released upon implantation. The drugs can be incorporated into the implant structure, for example, within the walls of the implant. The drug may be distributed throughout the wall of the implant. Alternatively or additionally, the implant may include a coating over the implant that includes the drug. The coating may include a polymer carrier with the drug distributed within the polymer.

The active agents can be incorporated into a carrier polymer which can include, but are not limited to, polylactide-based polymers such as poly(D,L-lactide) and copolymers thereof, polyglycolide-based polymers such as polyglycolide and copolymers thereof. Carrier polymers can also include other polyesters such as polycaprolactone, polyanhydrides such as poly(sebacic anhydride), polyhydroxyalkanoates such as poly(3-hydroxybutyrate), polyester-amide, hydrophilic polymers such as polyethylene glycol/oxide, and polyvinylpyrrolidone. Carrier polymers also include blends of the disclosed polymers and copolymers of the disclosed polymers. Additional carrier polymers include hydrogels made from polyethylene glycol, polyvinypyrolidone, polysaccharides, sugar, or copolymers thereof with a biodegradable polymer such as PDLLA, PGA, or another family of the carrier polymer.

The carrier polymer facilitates or provides controlled release of the active agents. The active agents may be released over a period of 1 day to 2 weeks, 2 weeks to 1 month, 1 to 2 months, 2 to 5 months, or greater than 5 months.

Stent slippage and migration with an airway lumen after implantation is a complication of current devices. A balloon expandable, bioresorbable scaffold can include geometric features that facilitate or assist in anchoring a scaffold in the airway lumen. As discussed above, the stent can also include a mucoadhesive coating that assists in securing the scaffold in place.

Anchoring of the scaffold can be facilitated by struts flaring out of plane during deployment, specifically in the region of the crests and troughs. This geometric feature of the scaffold could provide migration control by fixing the scaffold between the cartilaginous rings of the trachea.

Figure 5:
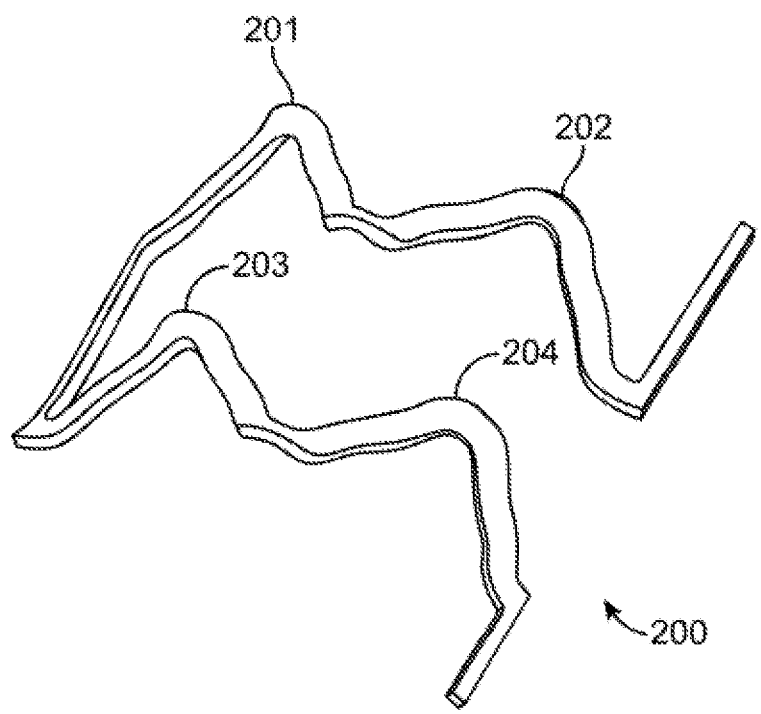
FIG. 5 depicts a section of a radially expanded scaffold showing crests or troughs that are flared outward.

FIG. 5 depicts a section 200 of a radially expanded scaffold showing crests or troughs 201-204 that are flared outward. The scaffold may be deployed so that the crests and troughs are positioned between the cartilaginous rings and the flares protrude outward. The flares reduce or limit the degree of axial migration through contact with the rings by acting as a hard stop. Such a scaffold may be removable due to drop in molecular weight and loss of strength with time. This will allow it to be manipulated and collapsed so that it may be removed from the airway. In the case where the scaffold would be targeted to eliminate the need for re-intervention, the polymer will soften but remain attached to the walls of the airway.

The tendency and degree of flaring is increased by certain design features. For example, the tendency for flaring increases as the ratio of the initial diameter of the scaffold or delivery diameter to the final expanded diameter decreases. The tendency and degree of flaring also depends on the aspect ratio of the scaffold strut, where the aspect ratio is the ratio of the radial strut thickness to the strut width. The tendency and degree of flaring increase as the aspect ratio decreases. The aspect ratio can be less than 0.8, less than 0.5, less than 0.2 or 0.2 to 0.5, 0.4 to 0.6, or 0.5 to 0.8.

The scaffold can be designed so that in a deployed state the axial distance between crests of adjacent rings can be the width or spacing of the cartilaginous rings. The flaring height can be the depth between the cartilaginous rings.

The radial thickness of a fenestrated or non-fenestrated stent may be 100 to 150 microns, 150 to 200 microns, 200 to 400 microns, 400 to 500 microns, 500 to 1000 microns, or 1000 to 2000 microns, or greater than 2000 microns.

"Molecular weight" refers to either number average molecular weight (Mn) or weight average molecular weight (Mw). References to molecular weight (MW) herein refer to either Mn or Mw, unless otherwise specified. The Mn may be as measured by Gel Permeation Chromatography with refractive index detection relative to polystyrene standards. Suitable mobile phase solvents are acetone, tetrahydrofuran, chloroform, 1,1,1-trichloroethane, 2,2,2-trifluoroethanol, and hexafluoro-2-propanol.

"Semi-crystalline polymer" and other terms relating to crystalline polymer may be as defined in Pure Appl. Chem., Vol. 83, No. 10, pp. 1831-1871, 2011. Semi-crystalline polymer refers to a polymer that has or can have regions of crystalline molecular structure and amorphous regions. The crystalline regions may be referred to as crystallites, lamella, or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility. The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The Tg of a polymer, unless otherwise specified, can refer to a polymer that is in a dry state or wet state. The wet state refers to a polymer exposed to blood, water, saline solution, or simulated body fluid. The Tg of the polymer in the wet state can correspond to soaking the polymer until it is saturated.

The "degree of crystallinity" may be expressed in terms of, we (mass fraction), $\phi_c$ (volume fraction) and refers to mass fraction or volume fraction of crystalline phase in a sample of polymer. The mass-fraction and the volume-fraction degrees of crystallinity are related by the equation, $w_c = \phi_c \rho/\rho_c$, where $\rho$ and $\rho c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry, (iii) mass density measurements, (iv) infrared spectroscopy (IR), (v) solid-state NMR spectroscopy, and (vi) vapor permeability.

"Stress" refers to force per unit area, as in the force acting through an area within a plane. Stress can be divided into components, normal and tangential to the plane, called normal stress and shear stress, respectively. Tensile stress, for example, is a normal component of stress applied that leads to expansion (increase in length). In addition, compressive stress is a normal component of stress applied to materials resulting in their compression (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress-strain curve at low strain in the linear region.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating an airway disorder in a patient in need of treatment thereof, comprising:
   providing a bioresorbable non-expandable stent; and
   maintaining an airway in a desired configuration by disposing the stent within the airway of a patient having an airway disorder,
   wherein an initial radial strength of the stent allows it to maintain the desired configuration of the airway to allow healing of the airway,
   wherein the radial strength of the stent decreases with time due to bioresorption of the stent allowing the airway to adjust from being artificially supported to a healed state without artificial support of the stent; and
   removing the stent from the airway at a prescribed time point through intervention after disposing the stent within the airway, wherein the stent is designed to have adequate axial strength at the prescribed time point to allow removal of the stent.

2. The method of claim 1, wherein the airway is selected from the group consisting of pharynx, larynx, and trachea.

3. The method of claim 1, wherein the stent comprises a variable diameter that conforms to the geometry of the airway.

4. The method of claim 1, wherein the airway disorder is selected from the group consisting of laryngotracheal stenosis, glottic stenosis, subglottic stenosis, bronchogenic tumors, tracheomalacia, bronchomalacia, tracheal trauma, a tracheal lesion, and stenosis that occurs following the resection of lesions in the airway.

5. A method of treating an airway disorder in a patient in need of treatment thereof, comprising:
   providing a bioresorbable radially expandable bioresorbable scaffold in a reduced delivery configuration mounted over a balloon;
   delivering the scaffold to an implant site in an airway, wherein the airway has a variable diameter;
   radially expanding the scaffold at the implant site within the airway by inflating the balloon; and
   expanding a dilatation balloon in specific regions of the scaffold not conforming to a wall of the airway for better apposition of the scaffold to the wall of the airway such that a diameter of the scaffold varies along with the variable diameter of the airway,
   wherein an initial radial strength of the scaffold allows it to maintain the airway in a desired configuration of the airway to allow healing,
   wherein the radial strength of the scaffold decreases with time due to bioresorption of the scaffold allowing the airway to adjust from being artificially supported to a healed state without artificial support of the scaffold.

6. The method of claim 5, wherein the airway is selected from the group consisting of pharynx, larynx, and trachea.

7. The method of claim 5, wherein the expanded scaffold conforms to an airway anatomy through variable expansion of the scaffold.

8. The method of claim 5, wherein the scaffold is not removed from the airway through intervention and is allowed to resorb completely away from the airway.

9. The method of claim 5, wherein the airway disorder is selected from the group consisting of laryngotracheal stenosis, glottic stenosis, subglottic stenosis, bronchogenic tumors, tracheomalacia, bronchomalacia, tracheal trauma, a tracheal lesion, and stenosis that occurs following the resection of lesions in the airway.

\* \* \* \* \*